(12) United States Patent
Koh et al.

(10) Patent No.: US 8,192,360 B2
(45) Date of Patent: Jun. 5, 2012

(54) IMPLANTABLE BODY FLUID ANALYZER

(75) Inventors: Steve Koh, South Pasadena, CA (US); Jonathan T. Losk, Sherman Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 1216 days.

(21) Appl. No.: 11/861,028

(22) Filed: Sep. 25, 2007

(65) Prior Publication Data
US 2009/0082652 A1 Mar. 26, 2009

(51) Int. Cl.
*A61B 5/00* (2006.01)
*C12M 1/00* (2006.01)

(52) U.S. Cl. ........ 600/309; 600/310; 600/317; 600/324; 600/325; 600/345; 435/283.1

(58) Field of Classification Search .................. 600/309, 600/310, 322, 342, 317, 324–326, 341; 435/283.1; 604/20, 165
See application file for complete search history.

(56) References Cited

U.S. PATENT DOCUMENTS

| 4,863,693 | A | * | 9/1989 | Howell ........................... 422/64 |
| 5,029,583 | A | * | 7/1991 | Meserol et al. ............... 600/316 |
| 5,176,881 | A | * | 1/1993 | Sepaniak et al. .............. 600/342 |
| 5,535,744 | A | * | 7/1996 | DiNino .......................... 600/322 |
| 6,001,067 | A |   | 12/1999 | Shults et al. |
| 6,267,724 | B1 | * | 7/2001 | Taylor ........................... 600/309 |
| 6,540,675 | B2 | * | 4/2003 | Aceti et al. ................... 600/309 |
| 6,741,877 | B1 |   | 5/2004 | Shults et al. |
| 7,004,928 | B2 | * | 2/2006 | Aceti et al. ................... 600/575 |
| 2004/0096959 | A1 | * | 5/2004 | Stiene et al. ............... 435/287.2 |
| 2005/0043894 | A1 |   | 2/2005 | Fernandez |
| 2005/0049472 | A1 |   | 3/2005 | Manda et al. |

FOREIGN PATENT DOCUMENTS

| WO | WO 99/39629 | 8/1999 |
| WO | WO 2005/020797 A2 | 3/2005 |
| WO | WO 2005/020797 A3 | 3/2005 |

\* cited by examiner

*Primary Examiner* — Eric Winakur
*Assistant Examiner* — Chu Chuan (J J) Liu

(57) ABSTRACT

An exemplary implantable microarray device includes an inlet for a body fluid, a plurality of individual reaction cell arrays where each reaction cell array includes a series of reaction cells configured to receive the body fluid, a sensor array to sense a reaction result for an individual reaction cell array where the reaction result corresponds to a reaction between the body fluid and at least one reagent in each of the reaction cells of the individual reaction cell array and a positioning mechanism to position an individual reaction cell array with respect to the sensor array. Various other exemplary technologies are also disclosed.

20 Claims, 15 Drawing Sheets

IMPLANTABLE BODY FLUID ANALYZER

TECHNICAL FIELD

Subject matter presented herein relates generally to analysis of body fluid using an implantable device.

BACKGROUND

Recent advances in miniaturization by nano-technology have influenced drug development, gene analysis, blood analysis, etc. For example, commercial products lines have emerged that use so-called "Lab-on-a-Chip" technologies for various analyses and/or syntheses. Another common term used to describe activity and research in this field is Micro-Electro-Mechanical Systems (MEMS). Some MEMS Lab-on-a-Chip devices use semiconductor based array technology that allows for preparation and/or analysis of materials with nano-scale control.

While some technologies are exclusively for analyses, others allow for synthesis of large numbers of nano-structured materials. In addition, some technologies allow for testing of synthesized nano-structured materials using chip-based techniques. A microarray platform that includes arrays of microelectrodes may perform electrochemical syntheses and/or analyses. For example, a microarray platform may use controlling currents, voltages, etc., to influence structure and morphology of synthesized material and use the same microelectrodes for analysis of such material (e.g., using resistance or impedance). Consider polymerization of an organic molecule such as a pyrrole to form polypyrroles. A microarray platform may perform such polymerization in times of about 0.5 seconds to about 30 seconds using applied voltages of about 0.25 V to about 0.6 V varied across the array. Such a technique may form several hundred different compositions of polypyrroles using, for example, an array with several hundred reaction cells. The electronic, physical, and chemical properties of the resulting conducting polymers are known to depend on the methods and conditions used for synthesis. Further, such properties may be determined using the microelectrodes in an analysis mode.

A chip-based microarray may include integrated circuits (e.g., arrays of microelectrodes) that are individually addressable using embedded logic circuitry on the chip. Such a chip-based microarray may be used to digitally direct molecular assembly of chemicals in response to a digital command. For example, in the foregoing polypyrrole example, the logic may determine reaction conditions for each of the various reaction cells.

Some chip-based microarrays include so-called "porous reaction layer technology" to permit synthesis and attachment of biomolecules within the layer above a semiconductor surface. Some chip-based microarrays include so-called "virtual flask technology" to confine chemicals at each electrode within a defined virtual column or flask.

Exemplary devices and techniques disclosed herein may use such microarrays technologies and optionally other technologies, whether chip-based or otherwise, to perform analyses and/or syntheses within a patient. In particular, such exemplary devices may perform techniques that allow for analysis of body fluid, communication of analysis results (e.g., to another device whether implanted or external to the patient), drug syntheses, control of analyses, etc. Various exemplary devices and techniques use state-based analysis techniques for robust operation.

SUMMARY

An exemplary implantable microarray device includes an inlet for a body fluid, a plurality of individual reaction cell arrays where each reaction cell array includes a series of reaction cells configured to receive the body fluid, a sensor array to sense a reaction result for an individual reaction cell array where the reaction result corresponds to a reaction between the body fluid and at least one reagent in each of the reaction cells of the individual reaction cell array and a positioning mechanism to position an individual reaction cell array with respect to the sensor array. Various other exemplary technologies are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
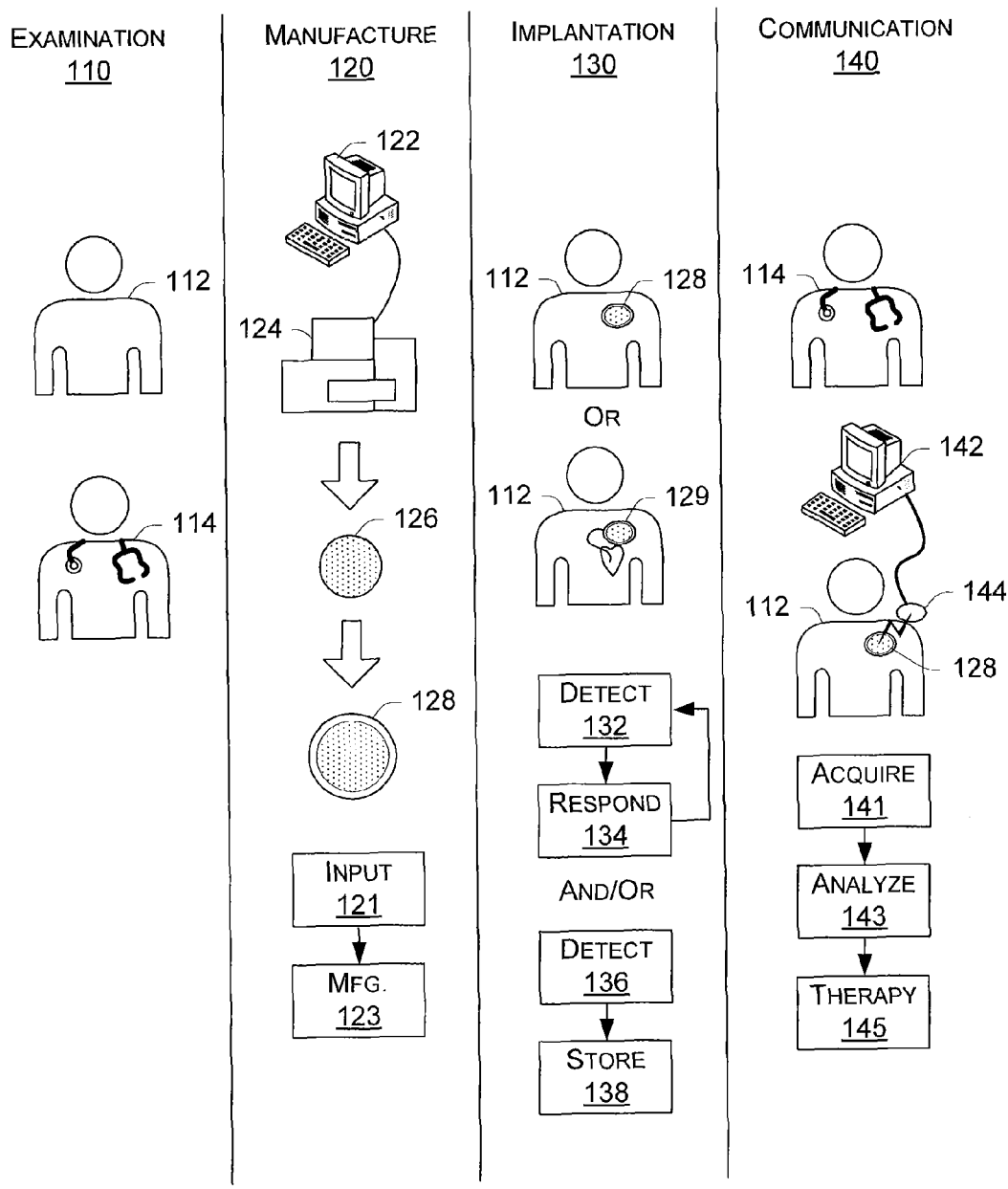
FIG. 1 is a diagram of various phases of an exemplary method that uses an implantable microarray device.

FIG. 1 shows an exemplary method 100 that includes implanting a microarray device 128 in a patient 112. The method 100 commences in an examination phase 110 where a clinician 114 examines the patient 112. The examination may include a physical examination, a questionnaire, lab tests of body fluids or specimens, performance tests, tests typically used to determine cardiac condition, etc. After examination 110, the method 100 continues in a manufacture phase 120.

The manufacture phase 120 includes inputting patient information 121 to a computing device 122 for purposes of manufacturing 123 a microarray 126. In this example, the computing device 120 includes an algorithm to determine one or more microarray parameters for production of the microarray 126 by appropriate manufacturing equipment 124. The one or more parameters may relate to number of analyses, frequency of analyses, expected range of a result of an analysis, type and use of state-based analysis (e.g., Boolean, binary, etc.), use of an analysis for control action, etc. For example, if the examination phase 110 determines that a patient is at risk for a heart attack, then the manufacture phase 120 may produce an array with one or more reaction cells to analyze hormones such as atrial natriuretic hormone (ANP) and B-type natriuretic peptide (BNP), which coordinate heart function with blood vessels and the kidneys. After manufacture of the microarray 126, the microarray 126 may be assembled with appropriate circuitry and mechanisms to form an implantable microarray device 128. The implantable microarray device 128 may include circuitry and mechanisms to perform any of a variety of tasks, optionally including cardiac pacemaker tasks, cardiac defibrillation tasks, neural stimulation tasks, muscle stimulation tasks, etc. For example, while the device 128 may be solely for analysis of body fluid or solely for production of a pharmaceutical or biomolecule, combinations of analysis, production and other tasks are possible for purposes of cardiac therapy, obesity therapy, gene therapy, depression therapy, Parkinson's therapy, etc.

The method 100 includes an implantation phase 130 where a microarray device 128 is implanted in the body of the patient 112. The device 128 may be positioned as appropriate and may include one or more delivery and/or sampling mechanisms to deliver a microarray formed product to the body and/or to acquire a sample from the body for analysis by the microarray. In another example, a device 129 is shown in association with the heart of the patient 112 where the device 129 includes the microarray 126. In this example, the device 129 may be configured to detect a cardiac arrhythmia 132 and to respond accordingly 134. Detection may occur using a lead-based electrode(s) or surface electrode(s). A response may include sampling blood to perform a BNP analysis. In turn, the device 129 may, where so configured, deliver stimulation therapy to the heart or deliver a drug to the heart. A closed-loop may exist where further detection occurs after a response. Various exemplary devices discussed herein may implement a detect and response method where the detection and/or the response may rely on an implantable microarray device.

Also shown in the implantation phase 130 is a method that includes detection 136 followed by storage 138. In this example, the detection may occur as in the detection block 132. The storage block 138 can store information regarding a detected event and/or acquired information used for detection. A method may include detection, storage and response where the response occurs immediately after detection or at a later time (e.g., according to a schedule, etc.).

The method 100 further includes a communication phase 140 that may be used to acquire information 141 from an implantable microarray device 128 and/or program the implantable microarray device 128. A clinician 114 may use a computing device 142 and communication circuitry 144 to acquire information 141 from the microarray device 128 as implanted in a patient 112. The acquired information may be analyzed 143 and the results of the analysis used to prescribe or adjust a therapy 145. The results of the analysis may be used additionally or alternatively to program the microarray device 128, for example, to detect concentrations of a blood component more or less frequently, to detect concentrations in a different range, to detect concentrations of a blood component not previously detected, etc. For example, a microarray 126 may include many different reaction cells that may be selected based on a control signal or state. Consider a blood component concentration that lies within an initial given range and later exceeds this range. Accordingly, control logic (internal or external to the device 128) may cause the device 128 to use reactions cells for a more appropriate concentration range. Hence, a microarray may include a variety of reaction cells where only certain reaction cells are used at any given time.

Figure 2:
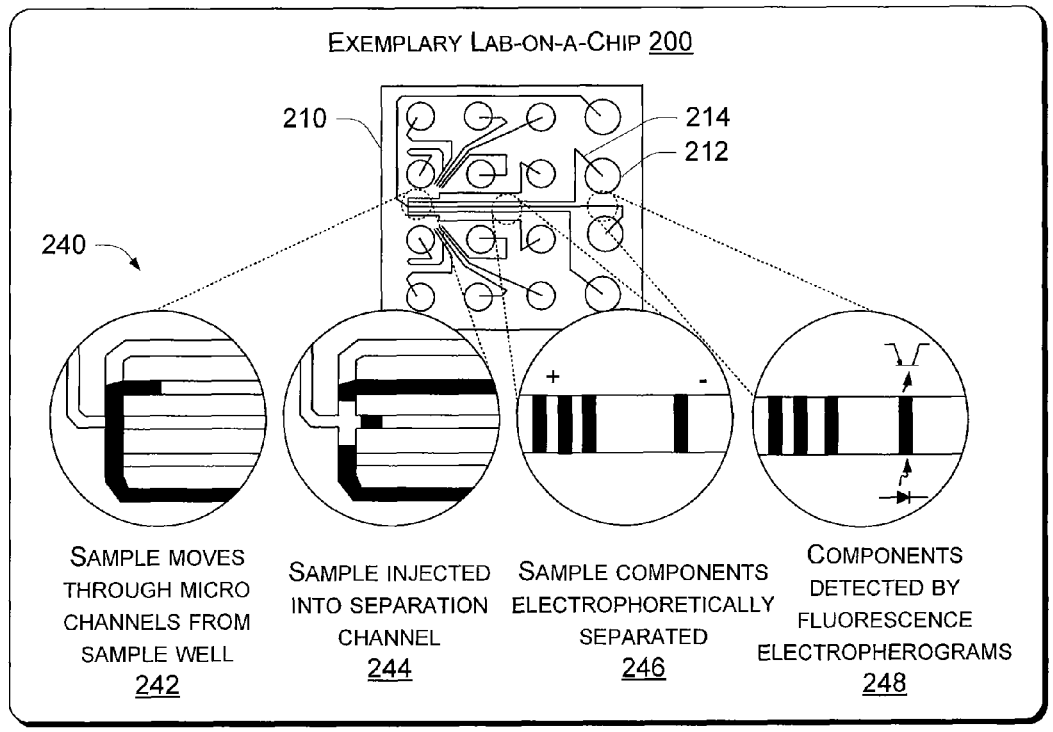
FIG. 2 is a diagram of an exemplary lab-on-a-chip device suitable for use in an implantable device.

An exemplary microarray may be chip-based. FIG. 2 shows a commercially available "Lab-on-Chip" microarray 200. The microarray 200 includes a chip 210 with various cells 212 and conduits 214. The microarray 200 may analyze samples according to a method 240. In a distribution step 242, a sample moves from a sample cell or well 212 through conduits or microchannels 214. In an injection step 244, a portion of the sample is injected into a separation channel for performing electrophoretic separation. As a separation step 246 separates the injected sample electrophoretically, a detection step 248 detects various separated components of the sample using fluorescence electropherograms (i.e., a recording of separated components of a mixture produced by electrophoresis). In this example, the chip 210 includes circuitry to perform fluorescence analysis. In the field of organic luminescence, the term fluorescence denotes a luminescence which occurs when a molecule makes an allowed optical transition. Thus, the chip 210 may include an emitter to supply electromagnetic radiation (e.g., ultraviolet radiation) that can excite an electron to a higher energy state and include a detector to detect energy released by the electron upon return to a lower energy state.

Figure 3:
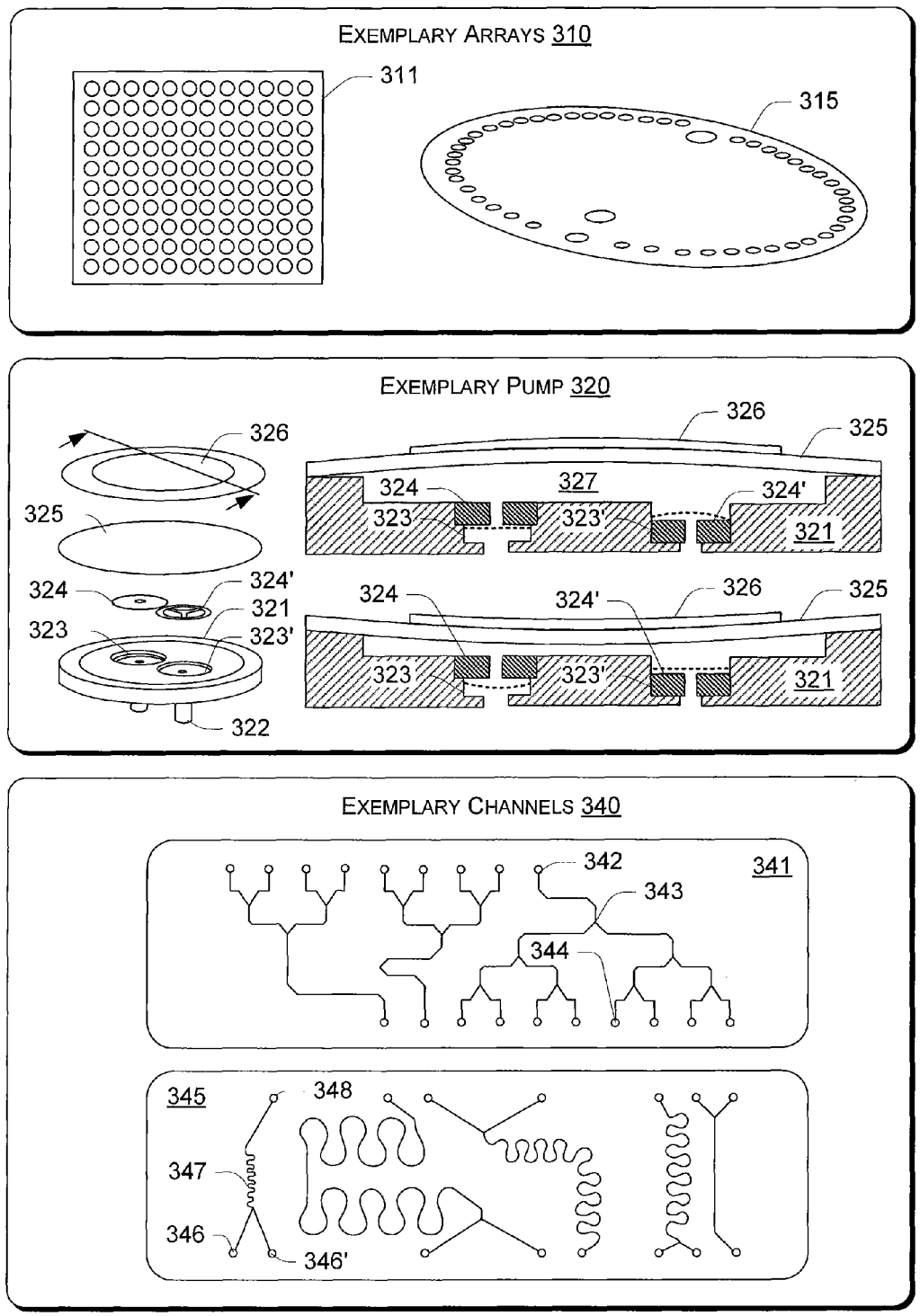
FIG. 3 is a diagram of exemplary arrays, an exemplary pump and exemplary channels suitable for use in an implantable device.

FIG. 3 shows arrays 310, a pump 320 and channels 340 for use in microarray applications. A microarray may be of any suitable shape such as rectangular 311 or circular 315. A microarray may include any number of cells and the cells may include feed cells (e.g., sample, reagent, wash, etc.), reaction cells and/or waste cells. Any individual cell may possess properties that facilitate analysis of a body fluid and/or production of a biomolecule. For example, a cell may be coated with one or more ligands (e.g., an ion, a molecule, or a molecular group that binds to another chemical entity to form a larger complex), may have a particular surface charge, may have surface properties that promote wetting or non-wetting, may be include a material that responds to a current, a potential, radiation (visible, IR, UV, etc.), etc.

An exemplary cell optionally includes a substrate in a dry state, for example, a state with low water activity (a low relative availability of water in the substrate). Low water activity can prevent chemical degradation of a substrate as well as biological degradation (e.g., bacteria usually require a water activity of at least 0.91 and fungi usually require a water activity of at least 0.7). In another example, an exemplary cell optionally includes a gel that facilitates analysis of a body fluid and/or production of a biomolecule. In either instance, the dry substrate or the gel may increase longevity of an active agent compared to having the active agent present in a liquid state. For example, in a dry state an active agent may have a longevity greater than or equal to the longevity of an exemplary implantable microarray device. According to an exemplary method, a body fluid is introduced to a reaction cell that includes an active agent in a dry state. In such an example, when the body fluid contacts the active agent, the water activity of the agent increases to facilitate reaction of the agent with the body fluid.

The exemplary pump 320 is a micro diaphragm pump for handling liquids and/or gasses. Flow rates may range from several microliters to a few millimeters per minute and such a pump may be self-priming and tolerant of gas bubbles. The pump 320 may be integrated into a lab-on-a-chip (see, e.g., device 200 of FIG. 2). The pump 320 includes a base 321 with conduits 322, 322' that provide paths to individual wells 323, 323' where one well acts as an inlet well and the other acts as an outlet well. The wells 323, 323' seat valve membranes 324, 324'. The pump 320 uses a pumping mechanism that relies on a pump membrane 325 and an actuator 326, which may be a piezoelectric actuator. As the actuator 326 actuates the membrane 325, a pump chamber 327 expands or contracts to thereby introduce pressure differentials that cause fluid to enter the chamber 327 via the inlet well or cause fluid to exit the chamber 327 via the outlet well.

The exemplary channels 340 include splitter channels 341 and mixing channels 345. The splitter channels 341 may split a material from a feed cell 342 into any number of separate channels, which may lead to individual reaction cells 344. A splitter channel may be manufactured from a cyclo-olefin copolymer (COC), which combines good optical properties with biocompatibility and good chemical resistance to most acids and bases. Other materials of manufacture are also possible.

An exemplary method uses a pump to move fluid into an implantable microarray device where splitter channels divide the fluid into smaller volumes. Splitter channels may rely on capillary action where gravity force has little effect on short distance fluid transfer. For example, capillary action may be used to move fluid from a feed cell into individual reaction cells. A reaction cell may include a substrate, a buffer, a reagent, etc., that interacts with the fluid introduced via a splitter channel. While the example of FIG. 3 shows individual cells 344 of approximately equal size, depending on reaction, etc., required volume may differ from cell to cell. Hence, a microarray may include various sizes of cells.

With respect to the mixer channels 345, while various arrangements are possible, a mixer channel typically includes a plurality of feeds cells or points 346, 346', a mixer section 347 and at least one outlet cell or point 348. A mixing mechanism may rely on a critical flow velocity in a succession of serpentines to form eddies that, in turn, cause mixing. A mixer channel may be primed with a material (e.g., solid, fluid or gas) that mixes with fluid from a feed well.

Figure 4:
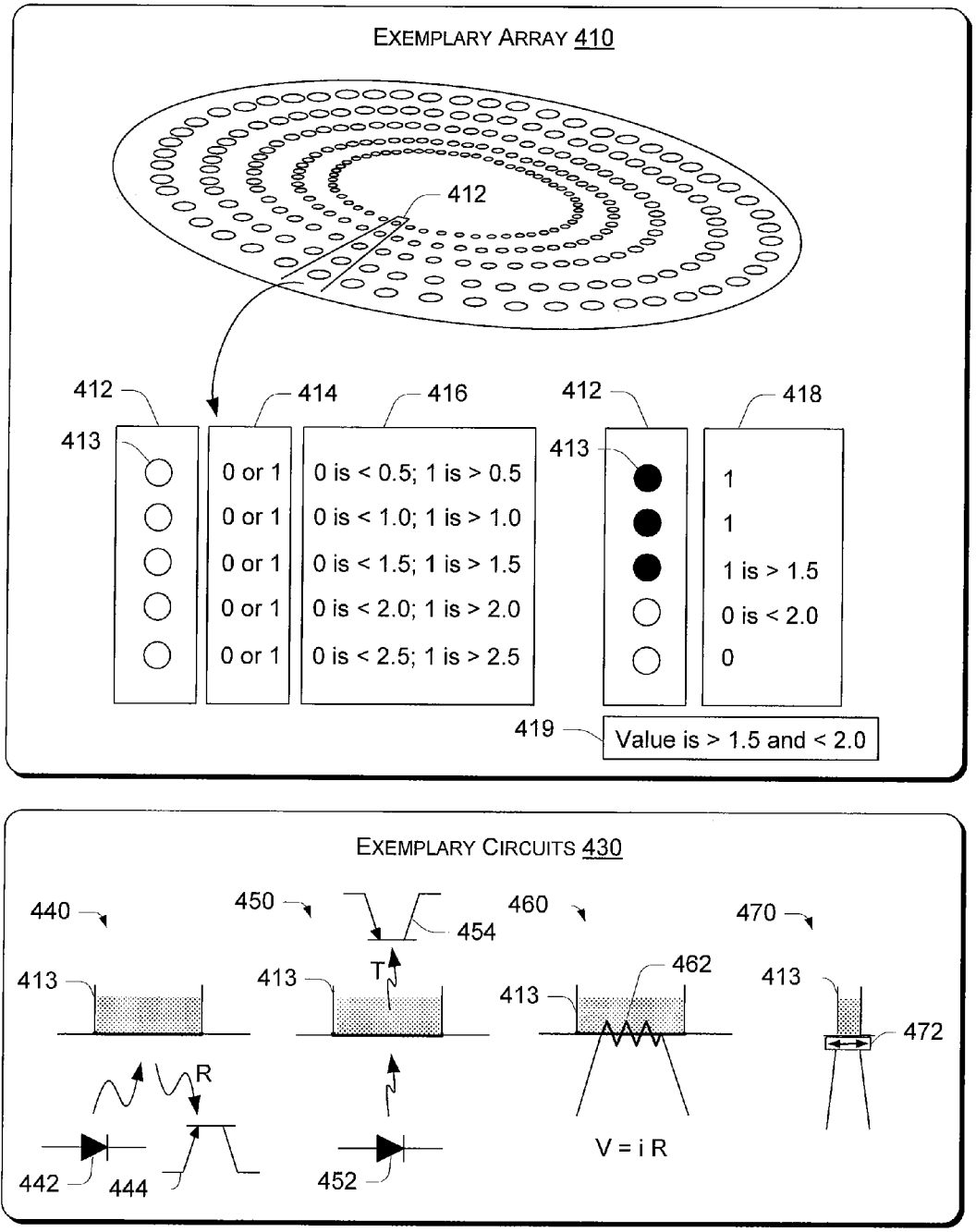
FIG. 4 is a diagram of an exemplary array and exemplary circuits suitable for use in an implantable device.

FIG. 4 shows an exemplary array 410 that includes cells 413 arranged in concentric circles. Along a radius a cell group 412 may be defined and used to perform a test or analysis. For example, a cell group 412 includes five individual cells 413. A reaction mechanism may allow each cell 413 to assume a binary state value (e.g., 0 or 1) as indicated by the values 414. However, the cell group 412 may be structured in a manner whereby each individual cell corresponds to a different reaction result. For example, the cell group 412 may include five cells where the first cell changes state at a concentration of 0.5, where the second cell changes state at a concentration of 1.0, where the third cell changes state at a concentration of 1.5, where the fourth cell changes state at a concentration of 2.0 and where the fifth cell changes state at a concentration of 2.5. Consider a scenario where a sample is introduced to the cell group 412, a reaction occurs and the individual cells 413 assume a binary state value as follows: [1 1 1 0 0]. In this example, the binary states of the cell group 412 may be interpreted as shown in block 418 and a result determined as in block 419, i.e., the value is between 1.5 and 2.0. As explained herein, such a result may be used for any of a variety of purposes.

An exemplary implantable microarray device may use electrical or optoelectrical mechanisms to assess a reaction result. FIG. 4 shows various exemplary circuits 430 including optoelectrical circuits 440 and 450 and electrical circuit 460 and 470. The optoelectrical circuit 440 relies at least in part on reflection. For example, an emitter 442 may emit and direct radiation toward a reaction cell 413 while a detector 444 may detect radiation reflected by the reaction cell 413. For example, if a reaction in a reaction cell causes a substantial change in the dielectric properties of the substance in the cell, then the cell, overall, may reflect radiation in a manner that can be detected by a detector. Adjustment of variables may allow for detection of reaction results in a binary manner.

The optoelectrical circuit 450 relies at least in part on transmittance. Principles such as reflectance and transmittance are used in spectrophotometry along with absorbance (e.g., Absorbance=$\log_{10}$ Transmittance$^{-1}$). As described herein, an optoelectrical circuit may be used in any of a variety of spectrophotometric manners (e.g., Beer's Law, Beer-Lambert Law, etc.) to assess reaction results or to acquire information about a cell in a microarray. As the circuit 450 relies at least in part on transmittance, an emitter 452 emits radiation that passes through the reaction cell 413. In turn, a detector 454 detects the transmitted radiation. In another example, a reflective surface exists on the reaction cell 413 that causes the radiation to make two passes through the reaction cell 413. In this manner, the detector 454 may be mounted on the same side of the reaction cell 413 as the emitter 452, which may simplify construction of an implantable microarray device.

The electrical circuit 460 relies on, for example, Ohm's Law (V=IR). The reaction cell 413 may change resistance or impedance 462 in response to a reaction or a solution or material in the reaction cell 413 may change resistance or impedance in response to a reaction. Alternatively, a reaction may produce an electrochemical reaction that can be detected by electrodes mounted in the reaction cell.

Figure 15:
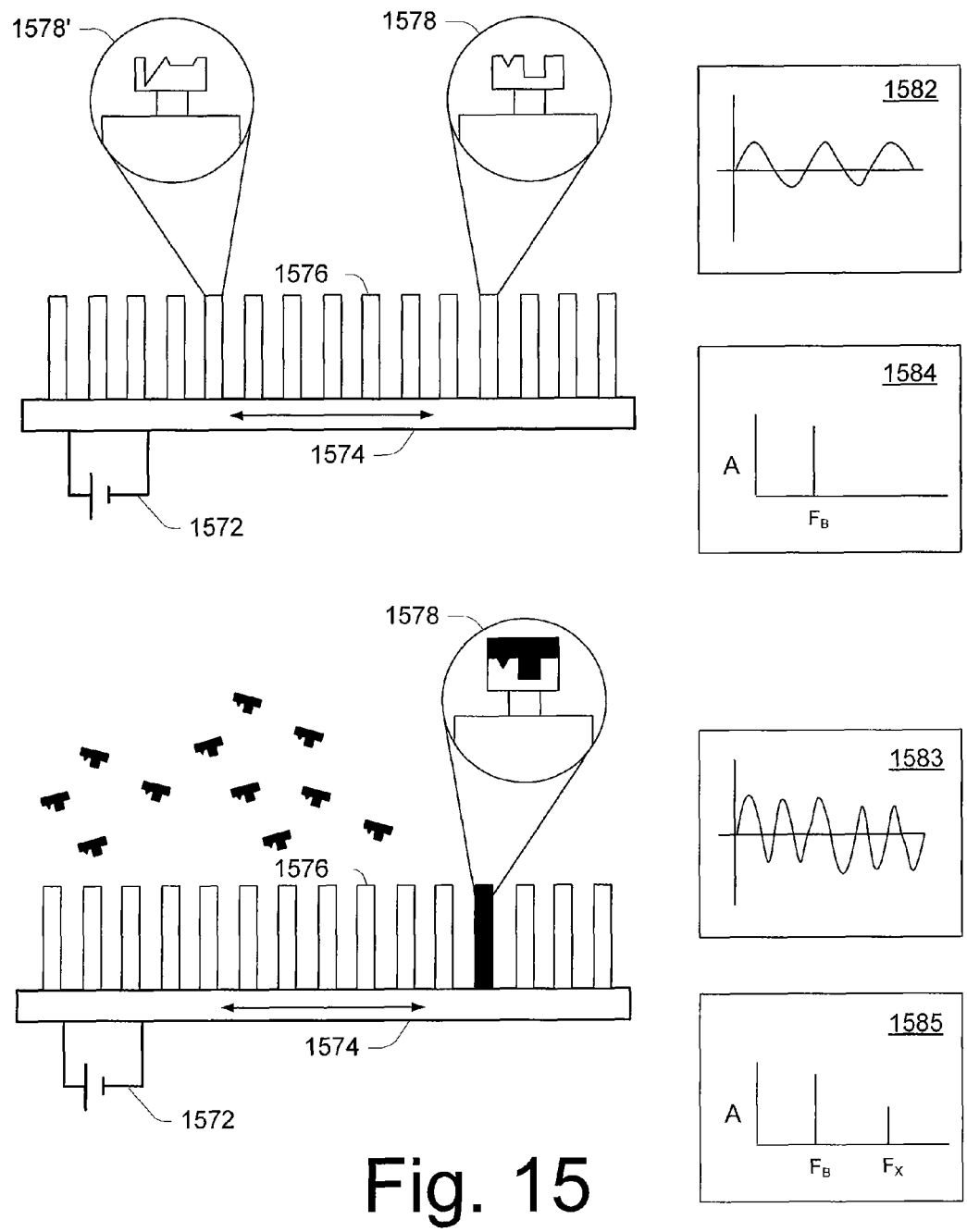
FIG. 15 is a diagram of a resonant frequency mechanism to detect conditions in the reaction cell.

The electrical circuit 470 relies on a resonant frequency mechanism to detect conditions in the reaction cell 413. For example, a reaction may form a complex that has a characteristic resonant frequency. Or the reaction may cause chemicals or constituents to adhere to the reaction cell 413 to give the reaction cell 413 a characteristic resonant frequency (a particular example is shown in FIG. 15). In the example of FIG. 4, the circuit includes a piezoelectric or similar device 472 to vibrate the reaction cell 413 and/or its contents. The circuit 470 may also monitor response via energy input to achieve a certain displacement or other vibrational characteristic.

Figure 5:
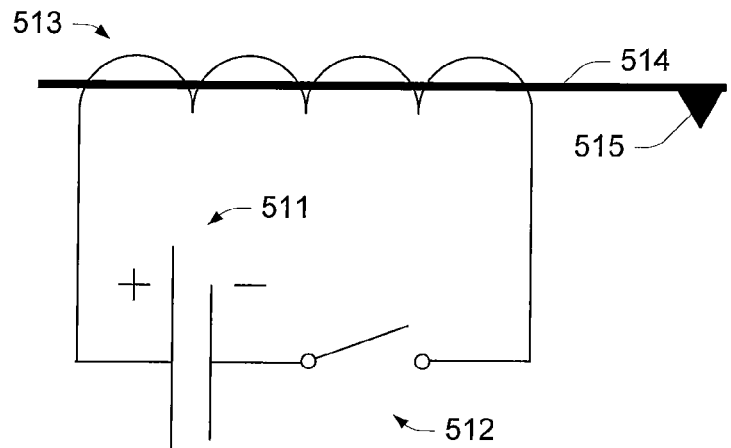
FIG. 5 is a diagram of an exemplary positioning mechanism that uses a solenoid.
Figure 5:
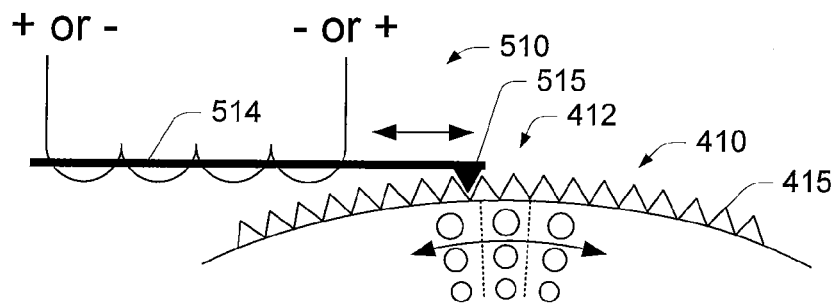
Figure 5:
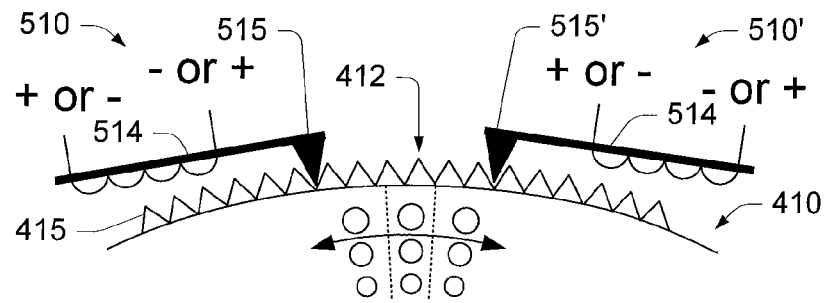

An exemplary microarray in an implantable device may be stationary or static or movable. Where movement of a microarray is required or desired, any of a variety of mechanisms may be used to move the microarray. FIG. 5 shows an exemplary positioning mechanism 510 that relies on a solenoid 513. A solenoid may be a loop of wire which produces a magnetic field when an electrical current is passed through it. Solenoids can create controlled magnetic fields and can be used as electromagnets. In the example of FIG. 5, a power source 511 and a switch 512 control the solenoid 513 field, which, in turn, causes movement of a metallic core 514. The metallic core 514 optionally includes a prong 515 or other feature that interacts with a feature of a microarray to thereby move the microarray.

An exemplary positioning arrangement 520 uses the solenoid-based mechanism 510 to move a circular microarray 410. The circular array 410 includes teeth 415 that mesh with the prong 515 of the metallic core 514. In this manner, the positioning mechanism 510 can position a group of cells 412 with respect to a feed line, an outlet line, a sensor or sensors, a reaction mechanism (e.g., heater, UV source, etc.), etc.

An exemplary positioning arrangement 530 uses two of the solenoid-based mechanisms 510 to move a circular microarray 410. The circular array 410 includes teeth 415 that mesh with the prongs 515 of respective metallic cores 514. In this manner, the positioning mechanism 510 can position a group of cells 412 with respect to a feed line, an outlet line, a sensor or sensors, a reaction mechanism (e.g., heater, UV source, etc.), etc.

A positioning mechanism may be controlled via a control signal of an implantable microarray device or via a signal transmitted to an implantable microarray device. Positioning may occur in response to a result, a patient request, a clinician request, a scheduled event, a physiologic condition (e.g., a cardiac condition), etc.

Figure 6:
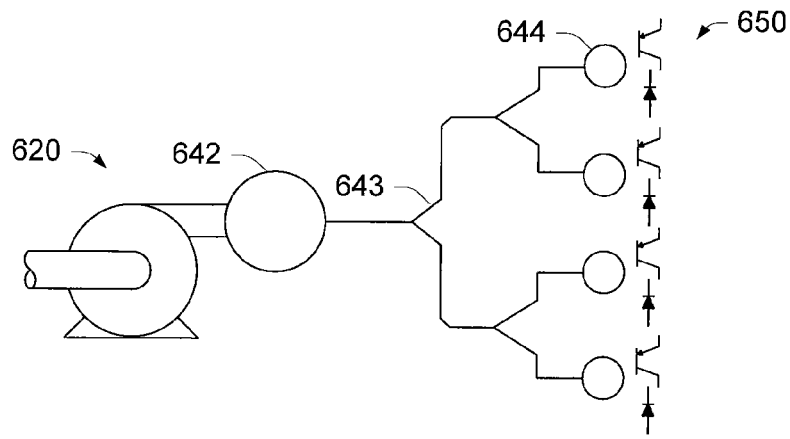
FIG. 6 is a diagram of various exemplary arrangements of pumps, feed cells, reaction cells and sensors suitable for use in an implantable device.
Figure 6:
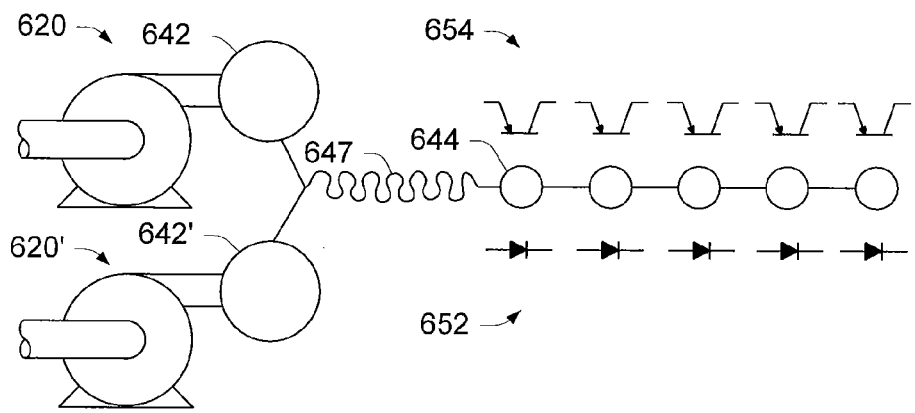
Figure 6:
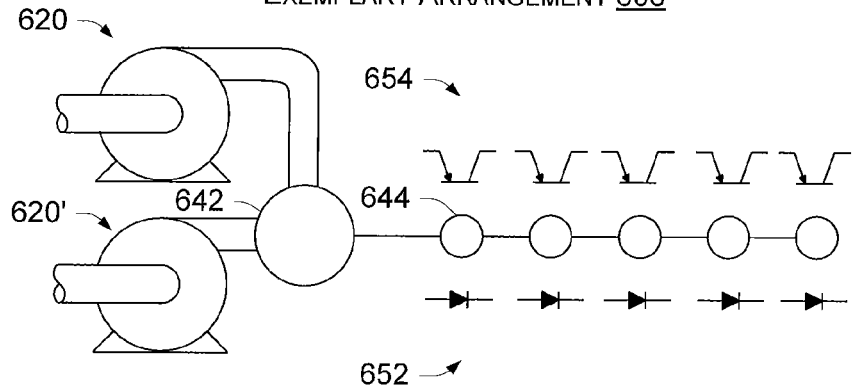

FIG. 6 shows various exemplary arrangements 602, 604 and 606. The arrangement 602 includes a pump 620 for pumping fluid to a feed cell 642. The feed cell 642 connects to a splitter channel 643 that splits a feed into four separate reaction cells 644. A series of sensors 650 provides for sensing reaction results in each of the four reaction cells 644.

The arrangement 604 includes two pumps 620, 620' for pumping fluid to respective feed cells 642, 642'. The feed cells 642, 642' connect to a mixing channel 647, which may use an in-line mixing element(s) or which may be shaped to create mixing eddies. The mixing channel 647 feeds a series of reaction cells 644, which may be connected in series and filled successively by pressure from the pump(s) 620, 620' or by capillary action. For example, capillary action may cause filling of the first cell, which, in turn, causes filling of the second cell, etc. A series of emitters 652 and detectors 654 provide for sensing reaction results in each of the reaction cells 644.

The arrangement 606 includes two pumps 620, 620' for pumping fluid to a feed cell 642. The feed cell 642 connects to a series of reaction cells 644. A series of emitters 652 and detectors 654 provide for sensing reaction results in each of the reaction cells 644. In this example, mixing may occur in the feed cell 642. Also, the pumps 620, 620' may be operated synchronously or asynchronously. For example, one pump may provide a reagent and the other pump may provide a body fluid. In any of the arrangements 602, 604, 606, valves or other mechanisms may be used to control flow of fluid. Such valves may be controlled using pressure, an electrical signals, a magnetic field, etc.

Figure 7:
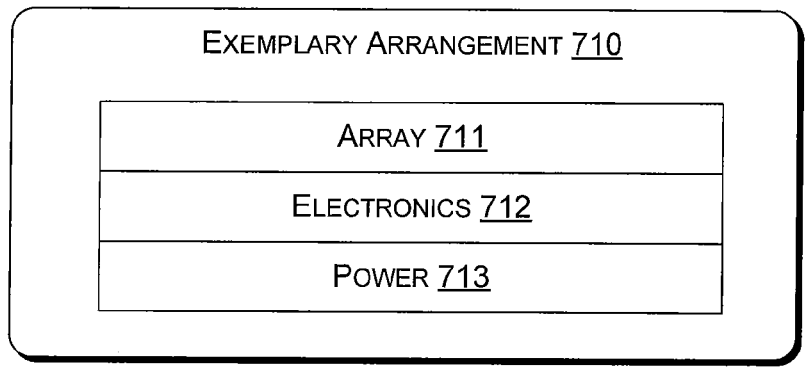
FIG. 7 is a diagram of various exemplary arrangements of components of an implantable device.
Figure 7:
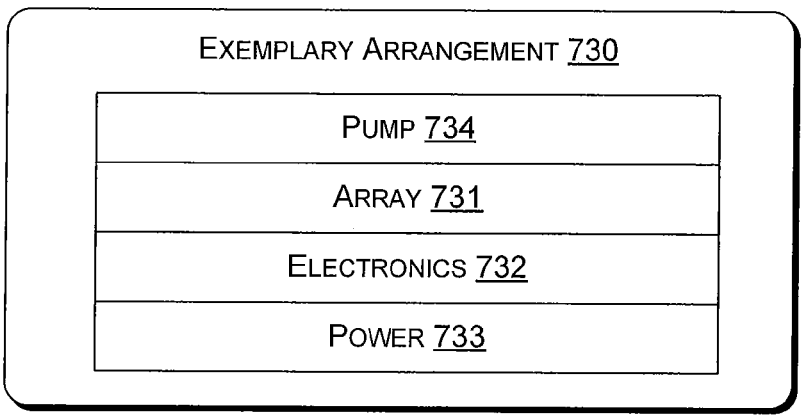
Figure 7:
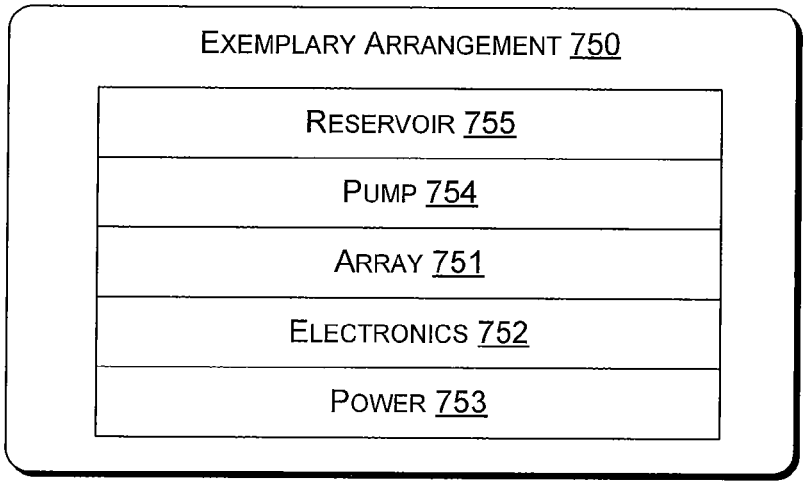

FIG. 7 shows various exemplary implantable microarray device arrangements 710, 730 and 750. The arrangement 710 includes an array 711, electronics 712 and power 713. In the arrangement 710, the array 711 may be stationary or movable via the electronics 712 and power 713. In general, the electronics 712 and power 713 provide for sensing reaction results of reaction cells of the array 711. Fluid may be introduced to the array 711 by an electrically controlled port or by another mechanism. For example, the device may include shuttered ports whereby an electrical mechanism opens or closes a port that provides fluid, directly or indirectly, to at least some reaction cells of the array 711. More specifically, a device may include a rotating disk with an opening that rotates to align with a port that feeds one or more reaction cells. Body fluid may enter the reaction cells via capillary action, pressure or by other means. With respect to pressure, a series of reaction cells may be sealed under vacuum and opened in vivo to draw in body fluid.

The arrangement 730 includes an array 731, electronics 732, power 733 and a pump 734. In this example, the pump 734 may be a diaphragm pump, such as the pump 230, or another type of pump. In general, types of pumps include centrifugal pumps, screw pumps, axial flow pumps (e.g., compressor wheel), rotary pumps (e.g., positive displacement including gear, lobe, sliding vane, etc.) and reciprocating pumps (e.g., piston in a cylinder including syringe type mechanisms and membrane pumps). A pump may include an outlet that is positionable with respect to an array or an array may be positionable with respect to an outlet of a pump.

The arrangement 750 includes an array 731, electronics 732, power 733, a pump 734 and a reservoir 755. While this example includes the pump 734, another type of arrangement may include a reservoir without a pump. In such an alternative arrangement, capillary action or another mechanism may allow for movement of fluid from a reservoir to an array or from an array to a reservoir. As already mentioned, a channel or a cell may be sealed under vacuum where upon opening, fluid is drawn into the channel or the cell.

A reservoir or reservoirs may hold any of a variety of materials, whether gaseous, liquid or solid. In general such materials are used for reactions (e.g., reactants, buffers, etc.) or for cleaning. A reservoir may hold waste from a reaction or a washing procedure.

Figure 8:
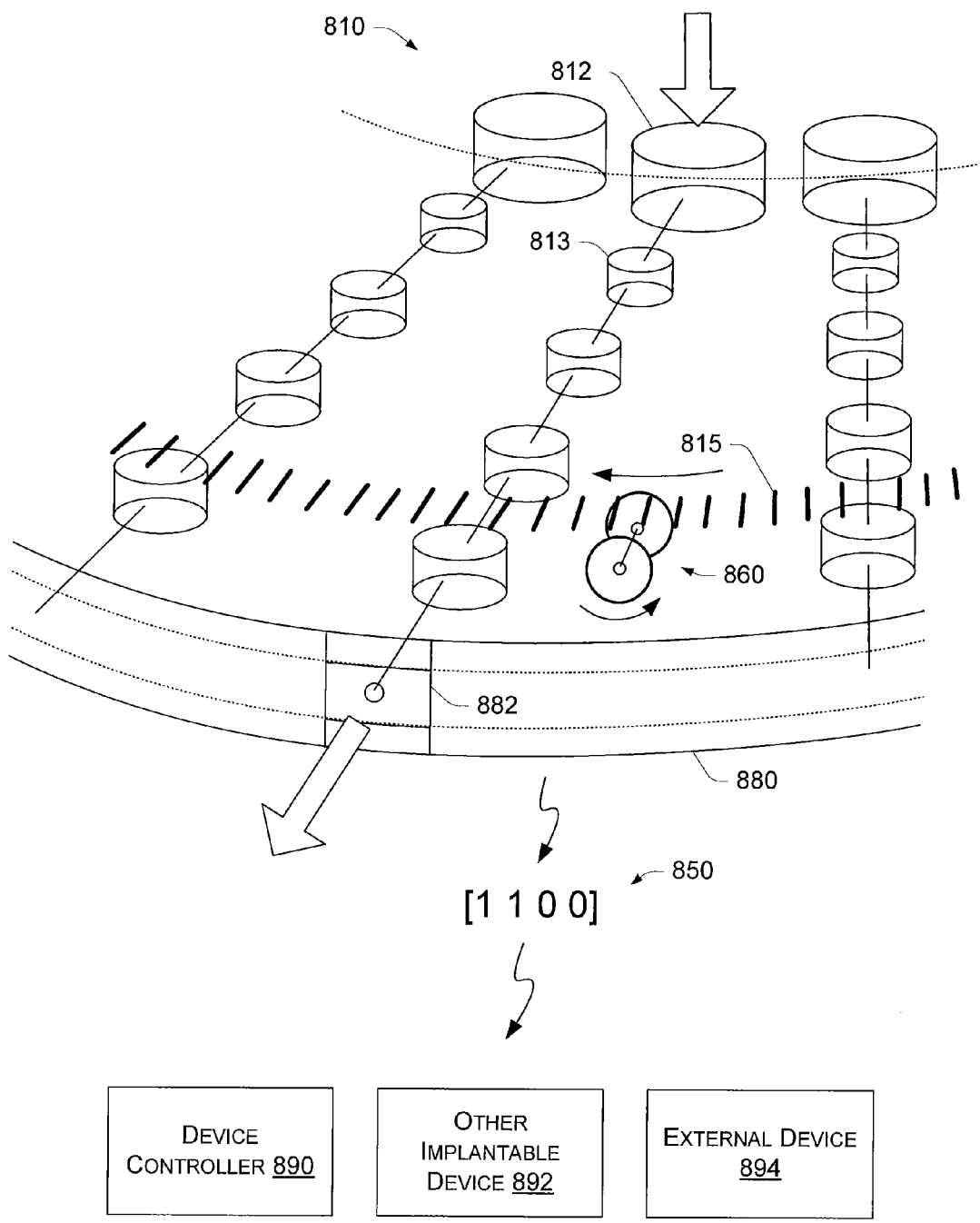
FIG. 8 is a diagram of an exemplary microarray for performing tests and outputting a binary signal or data as a test result.

FIG. 8 shows an exemplary arrangement 800 that includes a microarray 810 seated in a case or shell 880. The microarray 810 includes feed cells 812 and separate series of reaction cells 813. Positioning features 815 allow a positioning mechanism 860 to rotate the microarray 810 within the case 880. The positioning mechanism 860 may be driven by any of a variety of mechanisms (e.g., micromotor, solenoid, etc.). The case 880 includes an opening 882 that allows material to exit any particular series of reaction cells 813. The material may be gas, liquid or solid (e.g., particles in a fluid). The opening 882 may allow gas to exit the series of cells 813 upon filling with a fluid from the feed cell 812.

FIG. 8 does not show sensors, however, an implantable microarray device would include some type of sensing mechanism to sense reaction results for a reaction cell or cells (see, e.g., circuits 430 of FIG. 4).

In operation, the positioning mechanism 860 rotates the microarray 810 with respect to a feed line for filling feed cell 812. Capillary or other action causes fluid from the feed cell 812 to enter the series of reaction cells 812. Splitter channels and/or mixing channels may be used where appropriate. The reaction cells 813 may include a substance that participates in a reaction with the feed fluid. As already mentioned, a reaction cell may include a substance in a relatively dry state for purposes of longevity (e.g., water activity less than a desired amount such as less than 0.7). After or during reaction, a sensing mechanism senses reaction results for the individual cells of the series of reaction cells 813. In the example of FIG. 8, a binary result 850 is shown [1 1 0 0] for the four reaction cells 813.

A result may be transmitted to a device controller 890 of an implantable microarray device (e.g., for storage, for analysis or for control action), transmitted to another implantable device 892 (e.g., an obesity therapy device, a cardiac therapy device, etc.) and/or to an external device 894 (e.g., a programmer or other computing or data capture device).

Figure 9:
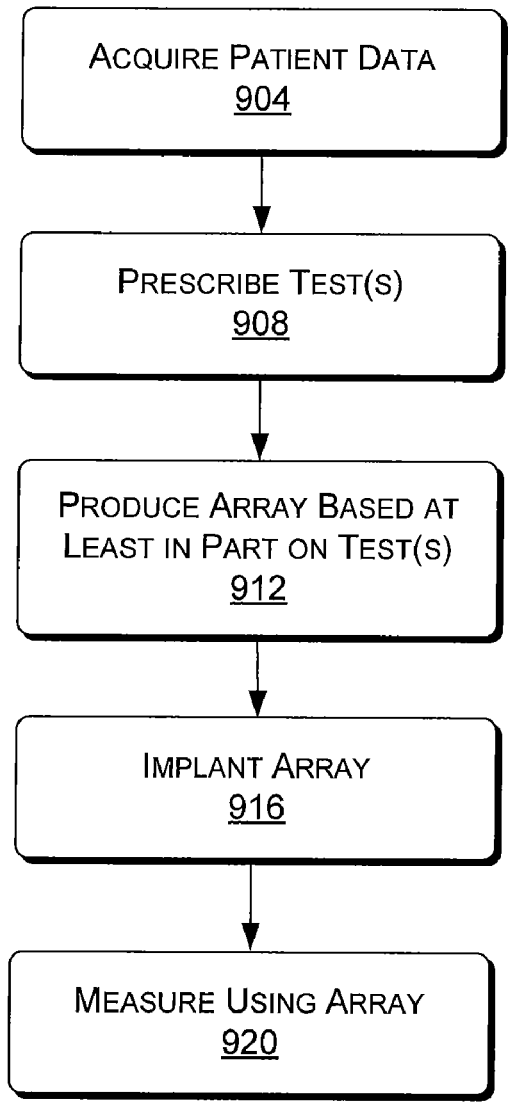
FIG. 9 is a diagram of an exemplary method for manufacturing and using a microarray in an implantable device.

FIGS. 2 through 8 show various exemplary devices and techniques. Such devices and techniques may be used in accordance with the method 100 of FIG. 1 or phases thereof. FIG. 9 shows an exemplary method 900 that corresponds approximately to the phases 110, 120, 130 and 140 of FIG. 1. According to the method 900, an acquisition block 904 acquires patient data. Acquisition of patient data may occur during an in-clinic examination, during a remote examination and/or through use of monitoring equipment. The acquired patient data 904 is then used in a prescription block 908 to prescribe a test or tests. The test or tests may be selected from a group of possible tests associated with a microarray for use in an implantable microarray device. A production block 912 then produces a microarray based at least in part on the prescribed test or tests.

Thus, the steps 904 through 912 allow for production of a microarray customized to a particular patient's needs. Such a microarray may then be combined with appropriate components (e.g., power source, electronics, pump, reservoir, etc.) to form an implantable microarray device. Components may include programmable memory for programming instructions associated with the prescribed test or tests. For example, each possible test may include a testing procedure with testing parameters such as test duration, test frequency, sample volume, result range, etc. Such parameters may be programmed as instructions on a processor-readable medium (e.g., a computer-readable medium).

An exemplary microarray may include a chip such as a smartcard or "subscriber identity module" (SIM). A typical cell phone SIM chip stores a key identifying a mobile subscriber and also contains storage space for text messages and a phone book. Such a chip may be used in an implantable microarray device for any of a variety of purposes including storage of test parameters, storage of communication information, storage of test results, etc.

Referring again to the method 900 of FIG. 9, after assembly of an implantable microarray device, implantation of the device in a patient occurs per the implantation block 916. The device may be implanted at any suitable location such as pectoral pocket, abdomen, etc. A device may include a lead to sample fluid or to deliver fluid to a particular region of the body (e.g., the digestive tract, the heart, the brain, the liver, the lungs, etc.). After implantation, a measurement block 920 performs one or more measurements using the implantable microarray device. As already mentioned, such measurements may be binary for robust operation and ease of storage, analysis and communication.

Figure 10:
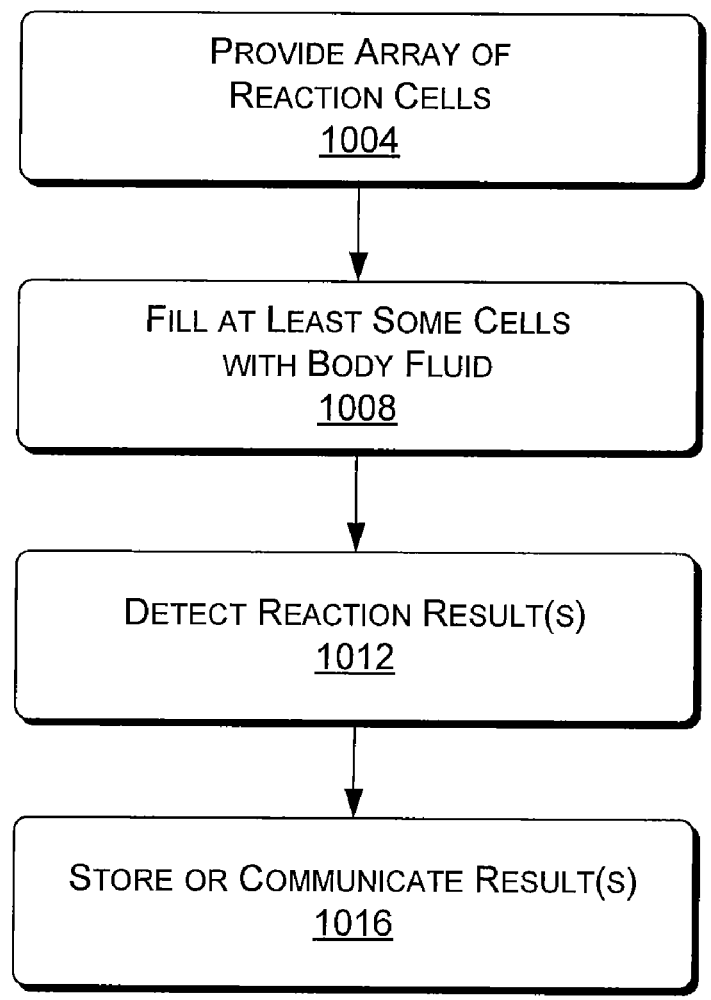
FIG. 10 is a diagram of an exemplary method for performing tests using an implantable microarray device.

FIG. 10 shows an exemplary method 1000 for using a microarray. The method 1000 commence in a provision block 1004 that provides an array of reaction cells. A fill block 1008 fills at least some of the reaction cells with a body fluid. Such filling may fill a reaction cell entirely or partially with a body fluid. Other fluid or fluids may also be in a reaction cell or introduced to a reaction cell. A detection block 1012 detects a reaction result or results for the reaction cells. A storage or communication block 1016 follows that stores or communicates the reaction result or results. As already mentioned, an implantable device may use a reaction result or results to control testing. For example, where a result is compared to a limit or other criterion or criteria, control logic may adjust one or more test parameters. Such control logic may adjust frequency of a test, selection of reaction cells, reaction time, etc.

Figure 11:
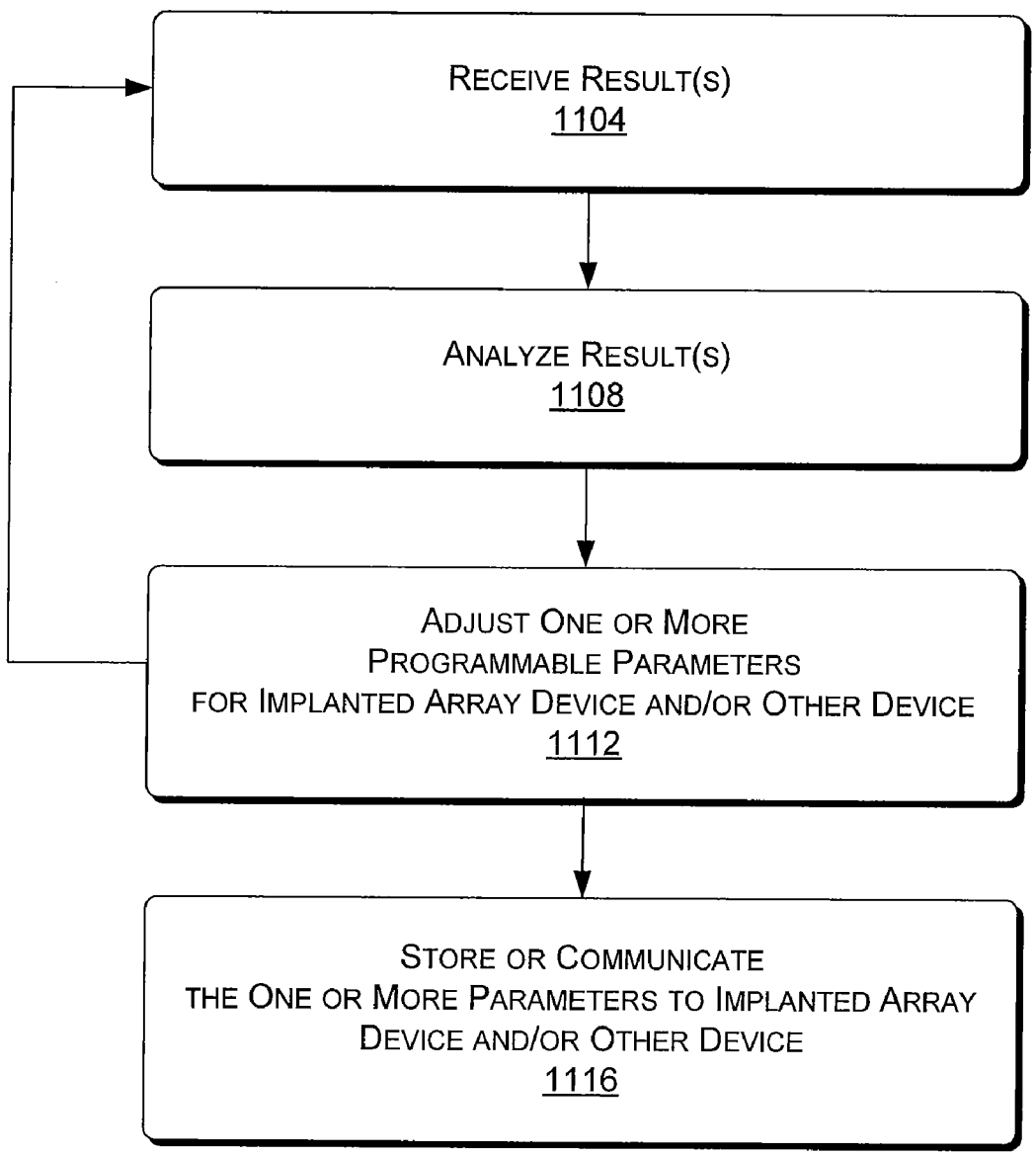
FIG. 11 is a diagram of an exemplary method for receiving and analyzing results acquired using a microarray implanted in a patient.

FIG. 11 shows an exemplary method 1100 for analysis of a test result or results. According to the method 1100, a reception block 1104 receives a result or results based on a test performed using a microarray and an analysis block 1108 analyzes the result or results. The result or results may be in the form of binary or other information generated by circuitry associated with the microarray (e.g., optical sensor, impedance sensor, etc.). The result or results may be communicated to or otherwise received by an external device, another implantable device and/or circuitry of an implantable microarray device associated with the microarray. With respect to external devices, the analysis 1108 may be performed using a device such as a desktop computer, an implantable device programmer, a PDA, etc. In some instances, an implantable microarray device includes circuitry for performing such an analysis (e.g., a processor, memory and processor-executable instructions to perform an analysis). Based at least in part on the analysis, an adjustment block 1112 adjusts one or more programmable parameters associated with the implantable microarray device and/or another implantable device (e.g., a drug delivery device, a cardiac therapy device, etc.).

Where the equipment used to perform the analysis and the parameter adjustment is external then the one or more adjusted parameters must be communicated to the implantable microarray device and/or other implantable device, as appropriate. Such communication may occur via telemetry circuitry commonly used in conventional implantable cardiac pacing devices. Where a device used to perform the analysis is another implantable device then the one or more adjusted parameters must be communicated to the implantable microarray device. Such communication may occur via wired or wireless techniques; noting that all wireless techniques require some amount of signal transmission through the body to reach an implantable device.

After the adjustment block 1112, the method 1100 may continue to the reception block 1104 and/or continue to a storage and/or communication block 1116 that stores and/or communicates the one or more parameters to an implantable microarray device and/or other implantable device. For example, where the analysis 1108 and the adjustment 1112 occur using features of an implantable microarray device and the adjustment pertains to this device then the device may implement the one or more adjusted parameters and the method 1100 may return to the reception block 1104.

While the method 1100 pertains to use of a test result or results to adjust a microarray device, such a result or results may be used for any of a variety of purposes. As already mentioned, a result or analysis thereof may be used by another implantable device or by an external device to better assess patient condition or to better deliver a patient therapy.

Figure 12:
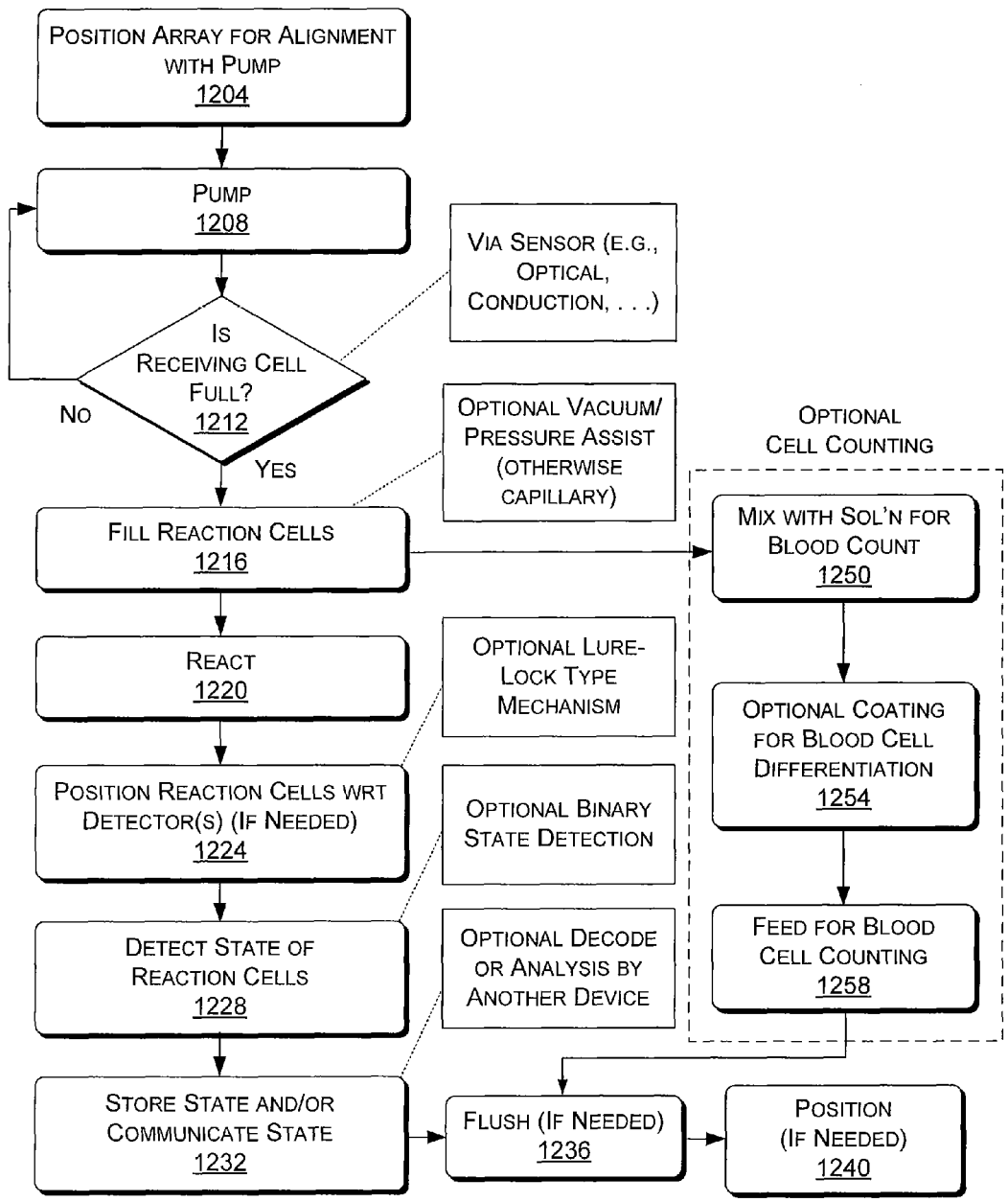
FIG. 12 is a diagram of an exemplary method for performing a test using a microarray.

FIG. 12 shows an exemplary method 1200 for operation of an implantable microarray device. The method 1200 commences in a positioning block 1204 that aligns a microarray with respect to a pump or pump line. After alignment, which may be detected using an electrical (e.g., contact switch) or optoelectrical mechanism (e.g., positioning to block or allow transmission of radiation), pumping occurs in a pump block 1208 to pump fluid to a receiving or feed cell. A decision block 1212 is used to decide whether the receiving cell is full or filled to a desired level. A sensor (e.g., electrical or optoelectrical) may be used to help make such a decision. If the decision block 1212 decides that the receiving cell is full, then the method 1200 continues in fill block 1216 to fill reaction cells, however, if the decision block 1212 decides that the receiving cell is not full, then the method 1200 continues at the pump block 1208 (closed-loop operation for filling of a receiving cell).

The fill block 1216 may optionally use vacuum assist and/or capillary action to fill one or more reaction cells. For example, the various splitter channels 341 of FIG. 3 may have dimensions that allow for capillary action, which may depend on fluid properties (e.g., viscosity, density, surface tension, etc.). Hence, where capillary action is used, a channel dimension may be selected on the basis of fluid properties to ensure adequate transport of a fluid. Properties of a channel material may be selected to facilitate or to inhibit capillary action. For example, attractive forces (hydrogen bonding) exist between glass materials (silicon dioxide) and water. Such forces facilitate capillary action, where the water can move up a thin capillary, against the force of gravity. Surface tension pulls neighboring water molecules along and the liquid climbs until the adhesive and cohesive forces are balanced by the force of gravity and/or other forces (e.g., friction losses). With respect to pressure assist, body pressure changes that occur with flow of blood, flow of air in the lungs, etc., may be used to move fluid in a microarray device. For example, intrathoracic pressure changes that occur during respiration can be sufficient to drive fluid in a microarray device. Further, for patients with a continuous positive airway pressure device (CPAP), changes can be programmed for pressure (e.g., during sleep) to accommodate particular fluid driving functions of the microarray device. In general, CPAP is known to increase intrathoracic pressure in a manner that reduces left ventricle afterload and unloads the inspiratory muscles of patients.

As an alternative to use of a reaction or reactions, an exemplary implantable microarray device may provide for blood cell count. Hence, after filling of the reaction cells or "blood count" cells, filling may entail mixing blood with a solution to facilitate blood count per the mixing block 1250. After such mixing, an optional coating material may be introduced for purposes of differentiating blood cells per the coating block 1254. For example, a chemical tag may be introduced that binds or otherwise associates with particular blood cells. Techniques used in flow cytometry such as staining immature RBCs with the supravital dyes, new methylene blue, brilliant cresyl blue, acridine orange or fluorescent dyes (e.g., 3,3'-dimethyloxacarbocyanine) that cause mature erythrocytes to fluoresce less than immature erythrocytes congruent to platelets to fluoresce less than leukocytes.

Per a feed block 1258, a blood cell mixture may be fed to a counting mechanism that counts blood cells. Such a mechanism may use electrical or optoelectrical techniques to detect presence or absence of blood cells in a fluid stream. A mechanism may use a window of known volume and size to count blood cells. After counting, the method 1200 may flush various cells or channels per a flush block 1236 and then position components, if needed, per a positioning block 1240 to thereby allow for subsequent testing or counting.

After filling of reaction cells 1216, a reaction block 1220 provides time for a reaction in a reaction cell and optionally initiates or terminates reaction in a reaction cell. With respect to initiation or termination, electricity and/or radiation may be used. For example, an electrochemical reaction may be terminated or controlled by applying a current to a reaction fluid, ultraviolet radiation is known to initiate or accelerate a variety of reactions and heat energy may control a reaction's thermodynamics and/or kinetics. Hence, an exemplary implantable microarray device may include one or more mechanisms to initiate, terminate or otherwise control a reaction.

A positioning block 1224 may be used, if needed, to position one or more reaction cells with respect to a detector or detectors. A detection block 1228 allows for detection of a reaction result or results. As already mentioned, reaction cells and reactions may be configured to allow for binary states and a binary result. After detection, a storage and/or communication block 1232 may store and/or communicate a result state for a reaction cell or a series of reaction cells. Analysis or decoding of the result or results may occur prior to, during or after storage and/or communication.

Depending on the configuration of an implantable microarray device, flushing (e.g., cleaning) of a channel, a receiving cell, a reaction cell, etc., may be required. Hence, the flush block 1236 may flush various components using, for example, a solution stored in a reservoir. Lastly, if required, a positioning block 1240 may position a pump, a channel, a cell, etc., to facilitate subsequent testing.

Figure 13:
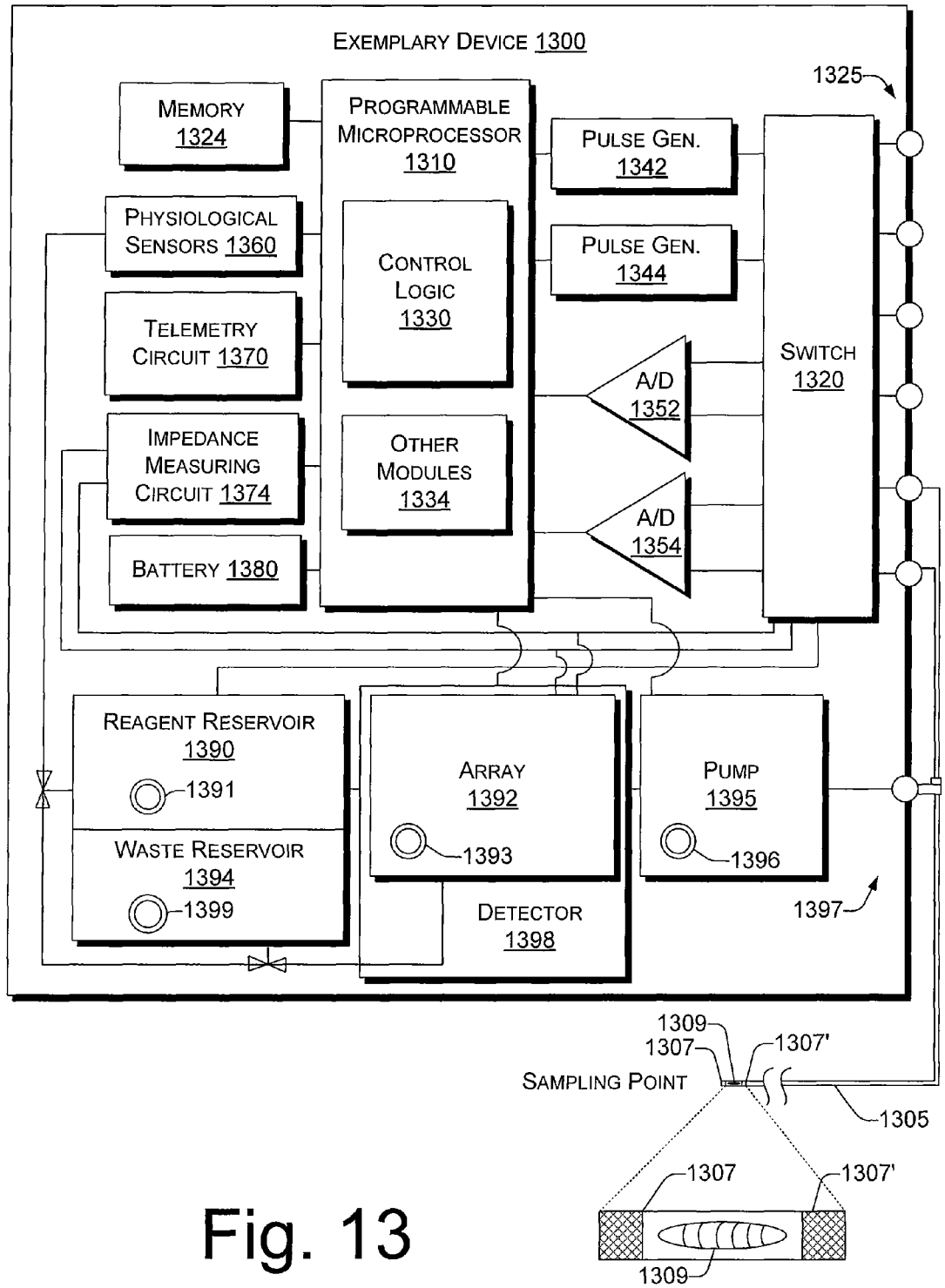
FIG. 13 is a diagram of an exemplary implantable microarray device that includes various features for performing tests and optionally delivering therapy.

FIG. 13 shows a block diagram of an exemplary implantable device capable of performing tests using a microarray. A basic device may include a processor, memory, one or more inputs, one or more outputs and control logic stored as instructions in the memory and operable in conjunction with the processor. The device 1300 includes various additional features.

The exemplary device 1300 includes a programmable microprocessor 1310 that can implement control logic 1330 and other instructional modules 1334. Information may be stored in memory 1324 and accessed by the programmable microprocessor 1310. For delivery of electrical energy, the device 1300 includes one or more pulse generators 1342, 1344. The pulse generators 1342, 1344 may rely on a switch 1320 for delivery of energy via one or more connectors 1325. While a device may include one or more integral leads, in general, a device includes one or more connectors for connecting a lead or leads to the device. More particularly, the connectors 1325 provide for electrically connecting one or more electrodes to the circuitry of the device 1300. In the example of FIG. 13, the switch 1320 may select an appropriate electrode configuration. An electrode configuration may include an electrode from one lead and an electrode from another lead, a case electrode and another electrode or electrodes from a single lead.

The device 1300 further includes one or more analog to digital converters 1352, 1354 for converting analog signals to digital signals or values. The processor 1310 may use a signal provided by one of the A/D converters 1352, 1354 to control a therapy or other process. A control signal from the processor 1310 may instruct the switch 1320 to select a particular electrode configuration for sensing electrical or other activity.

As already mentioned, a device may rely on binary states. Hence, the device 1300 may include digital acquisition circuitry to detect high and low states (e.g., 1 and 0) for a single input or for a series of inputs. For example, the array 1392 may include an associated detector 1398 that provides digital data directly to the microprocessor 1310.

The device may include one or more physiological sensors 1360. Such sensors may be housed within a case of the device 1300 (e.g., a motion sensor), include a surface mounted component, include a lead, include a remote sensor, etc. A sensor may provide a digital signal or an analog signal for use by the processor 1310 or other circuitry of the device 1300. A physiological sensor may provide a signal via one or more of the connectors 1325.

For purposes of communication with external or other implantable devices, the device 1300 includes a telemetry circuit 1370. The telemetry circuit 1370 may include one or more antennae for transmission and/or receipt of electromagnetic signals. Such a circuit may operate according to a specialized frequency or frequencies designated for medical devices. Various conventional implantable devices rely on an associated programmer, which is an typically an external computing device with a communication circuit suitable for communicating with an implantable device for purposes of data transfer, status checks, software download, etc. Where the circuit 1370 communicates with an implantable device or a device in electrical connection with a patient's body, then the body may be a conductive medium for transfer of information. For example, the circuit 1370 may be capable of communication with a specialized wristwatch where the body is relied upon as a conductor.

The device 1300 further includes an impedance measuring circuit 1374. Such a circuit may rely on instructions from the processor 1310. For example, the processor 1310 may instruct the circuit 1374 to provide a measured impedance for a particular electrode configuration of for a channel, a cell, etc., of the array 1392. Impedance information may be used by the processor 1310 for any of a variety of purposes. The processor 1310 may store impedance or other information to memory 1324 for later use or for transmission via the telemetry circuit 1370.

The device 1300 includes a power source, which is shown as a batter 1380 in the example of FIG. 13. The battery 1380 powers the processor 1310 and optionally other circuitry, as appropriate. In general, the battery 1380 provides power to the pulse generators 1342, 1344. Consequently, the battery 1380 provides for operation of circuitry for processing control logic, etc., and provides for energy to activate tissue. A lead-based sensor may connect to the device 1300 via one or more of the connectors 1325 and be powered by the battery 1380. The battery 1380 may be rechargeable, replaceable, etc.

The device 1300 includes a reservoir 1390 and an associated access port 1391, which may allow for insertion of a needle or other instrument. The port 1391 may allow for transdermal access to the reservoir 1390. The array 1392 includes an associated access port 1393, which may similarly for access to the array 1392. A pump 1395 may also include an access port 1396. For example, injection of a chemical into the port may allow the pump 1395 to pump the chemical to one or more locations.

A waste reservoir 1394 may allow for storage of waste fluid and include a port 1399 to extract the waste. For example, the microarray may operate using a reagent that, after use, is pumped to the waste reservoir 1394. Once the waste reservoir 1394 is full then a needle may be inserted into the port 1399 to extract the waste.

The device 1300 further includes a connector 1397 for connecting a conduit or lead 1305. In the example of FIG. 13, the lead 1305 includes two electrodes 1307, 1307' disposed adjacent an opening 1309. The opening 1309 connects to the pump 1395 via the connector 1397. Instructions from the processor 1310 may cause the pump 1395 to pump matter to and/or from the reservoir 1390 and/or the array 1392. In an alternative, matter may be introduced or removed via the port 1396. For example, the pump 1395 may operate to sample fluid via the opening 1309, which may then be extracted from the device 1300 via the port 1396. The arrangement may allow sampling of fluid and/or tissue from the body of a patient.

While a single lead is shown in FIG. 13, multiple leads may be used or one or more leads configured differently than the lead 1305. For example, a lead may connect to a patch where the patch affixes to the heart (e.g., a wall of the left ventricle). The patch may serve as a delivery mechanism for nutrients or drugs and may include one or more electrodes for any of a variety of purposes.

With respect to flow channels or conduits of the device 1300, microfluidic technologies may be employed. Microfluidic technologies generally include one or more channels with at least one dimension of less than about a few millimeters. Microfluidic technologies may transport body fluid samples, whole blood samples, bacterial cell suspensions, protein or antibody solutions, buffers, etc. Measurements of molecular diffusion coefficients, fluid viscosity, pH, enzyme reaction kinetics, etc., may be facilitated via microfluidic technologies. Other applications in microfluidics include capillary electrophoresis, isoelectric focusing, immunoassays, flow cytometry, cell manipulation, cell separation, cell patterning, chemical gradient formation, etc. Many applications have utility for clinical diagnostics.

With respect to pumping of matter, any of a variety of techniques may be used. For example, a pressure source (e.g., piezoelectric, mechanical, compressed gas, chemical, etc.), a mechanical pump, electrokinetic mechanisms, osmotic, electro-osmotic, etc., may be used. An exemplary device may use variations in pressure (e.g., intrapleural, intrathoracic, airway, etc.) that accompany respiration to promote flow or for pumping. For example, as the diaphragm contracts, the ribcage expands, which causes a decrease in intrathoracic pressure and flow of air into the lungs. With respect to intrapleural pressure, under normal conditions, it is always negative. The negative pressure between the two pleurae maintains partial lung expansion by keeping the lung pulled up against the chest wall. The degree of negativity, however, changes during respiration. During inhalation, the pressure is approximately −8 cm $H_2O$; during exhalation, approximately −4 cm $H_2O$. If a patient takes a deeper breath, the intrapleural pressure will be more negative. A balloon or compliant reservoir and valve arrangement may allow such variations in pressure to pump matter or to assist pumping of matter. Variations in pressure may be used to promote circulation or mixing of media.

The switch 1320 may be configured to allow for impedance or other measurements of the reservoir 1390, the array 1392, and/or the pump 1395. For example, impedance may indicate a change in condition of material in the reservoir 1390, a change in chemical composition or volume in the array 1392 and/or condition of the pump 1395 (e.g., primed or not primed).

One or more of the physiological sensors 1360 may be capable of sensing conditions of the reservoir 1390, the array 1392 and/or matter passing through the pump 1395.

While the device 1300 includes particular features, various exemplary devices, systems, methods, etc., may use or be implemented using a different device or devices with more or less features. For example, one device may provide fluidics while another device provides information to the fluidics device. The device 1300 may include features as associated with an insulin or other drug delivery device.

Figure 14:
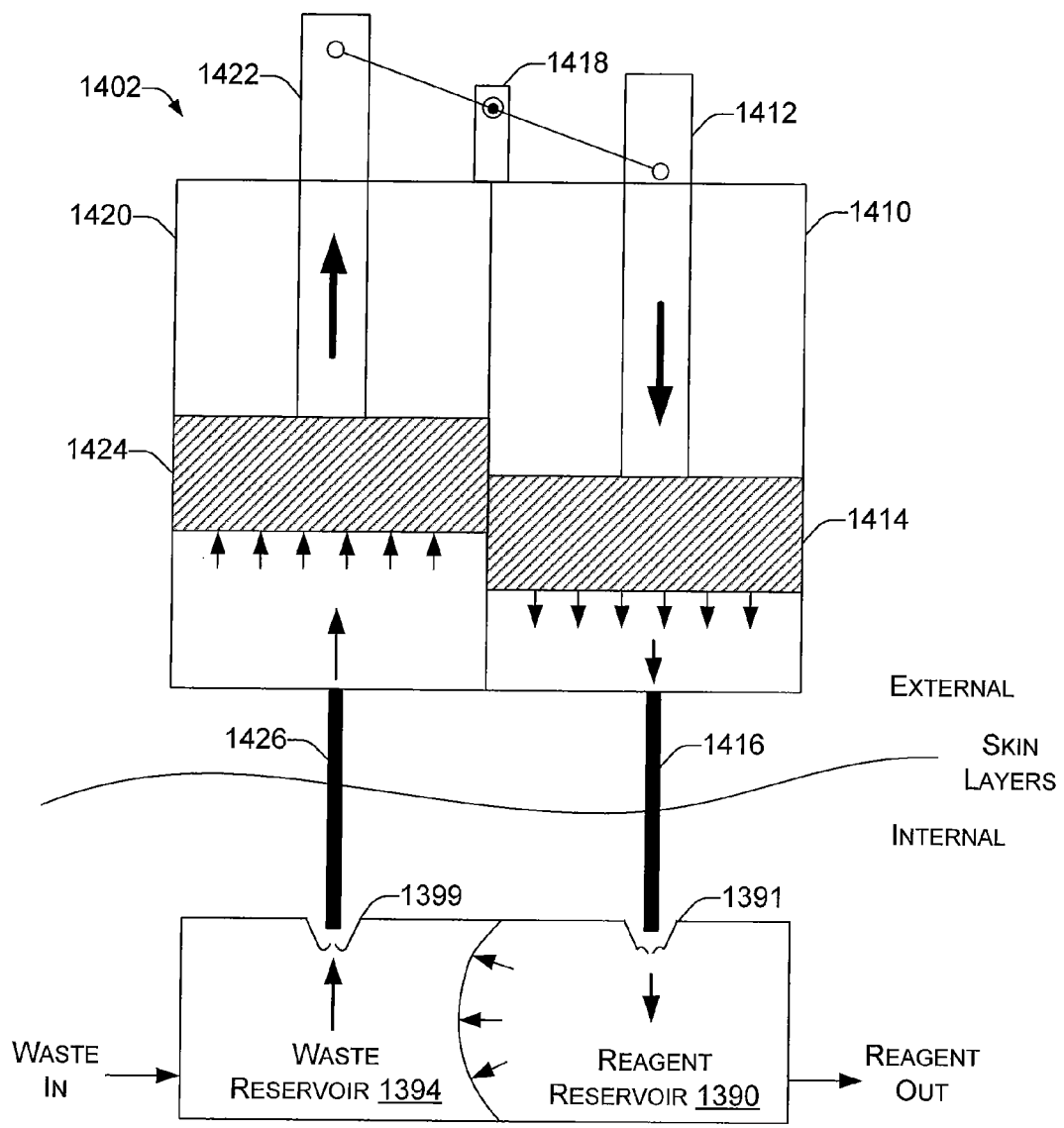
FIG. 14 is a diagram of an exemplary double syringe pump device for handling reagent and waste.

FIG. 14 shows a double syringe mechanism 1400 for filling a reagent reservoir and emptying a waste reservoir. In the example of FIG. 14, the reagent reservoir 1390 and the waste reservoir 1394 are separated by a flexible wall or membrane. As waste collects in the waste reservoir 1394, the membrane expands to occupy space in the reagent reservoir 1390, which becomes available as reagent flows from the reagent reservoir 1390.

To fill the reagent reservoir 1390 and empty the waste reservoir 1394, a double syringe device 1402 is positioned with respect to a recessed reagent reservoir port 1391 and a recessed waste reservoir port 1399. The recessed configuration of the ports 1391, 1399 assists in receipt or insertion of a filling conduit 1416 and a receiving conduit 1426 of the device 1402.

The double syringe device 1402 includes two barrels or chambers 1410 and 1420 where each chamber is fitted with a piston head 1414, 1424. In the example of FIG. 14, a respective shaft 1412, 1422 is connected to each piston head 1414, 1424 where a pivot mechanism 1418 couples movement of the two shafts 1412, 1422; hence, when one shaft moves, the other moves in an opposite direction.

The right side chamber 1410 is configured for filling the reagent reservoir 1390 where downward movement of the shaft 1412 drives the piston head 1414 and causes reagent to flow via the filling conduit 1416 (e.g., a needle) to the reagent reservoir 1390. As the reagent reservoir 1390 fills, the reagent exerts force on the membrane separating the two reservoirs, which, in turn, causes waste to exit the waste reservoir 1394 via the receiving conduit 1426 and enter the chamber 1420. In general, the pivot mechanism 1418 assists upward movement of the piston head 1424 to more readily remove waste from the waste reservoir 1394 and retain the waste within the chamber 1420.

An exemplary double syringe device, for use with an implantable device includes, a reagent barrel fitted with a reagent conduit, a waste barrel fitted with a waste conduit, a reagent barrel piston mounted to a shaft, a waste barrel piston mounted to a shaft and a pivot mechanism coupling movement of the reagent barrel piston and the waste barrel piston such that movement of the reagent barrel piston to expel reagent from the reagent barrel to an implantable device via the reagent conduit causes movement of the waste barrel piston to assist receipt of waste from the implantable device via the waste conduit.

FIG. 15 shows an exemplary resonant frequency mechanism 1500 for use in a microarray device. As mentioned, the mechanism 470 of FIG. 4 may include features of the mechanism 1500. The mechanism 1500 includes a piezoelectric circuit 1572 to oscillate a platform 1574 to which posts 1576 are mounted. Each post includes a binding site 1578, 1578'. The binding sites 1578, 1578' may be the same or different. If the same, the mechanism aims to detect the presence of components that bind to the site; whereas, if different, the mechanism can detect the presence of more than one type of component. A plot 1582 shows a time series of a base frequency for the platform 1574 and posts 1576 when the sites 1578, 1578' are unbound. A frequency plot 1584 indicates that the assembly has a base frequency $F_B$. When components are introduced, some of the components may bind to the binding sites 1578, 1578', which, in turn, alters the frequency characteristics as shown in the plot 1583. An analysis plot 1585 of the time signal indicates that a second frequency, a bound frequency $F_X$ exists. Existence of the bound frequency indicates presence of a corresponding component and the amplitude of the frequency can indicate the amount of that component that has bound to the posts.

More generally, an exemplary implantable microarray device may perform tests for or related to any of the following: red blood cells, polycythemia (increased count), platelets, thrombocytopenia (decreased count), diabetes, blood glucose, PSA (prostate specific antigen e.g., elevated levels associated w/Prostate Cancer), TSH (Thyrotropin), hyperthyroidism, hypothyroidism, liver/kidney disorders, electrolytes, sodium, blood urea nitrogen, creatinine, HDL (high density lipoprotein e.g., good cholesterol), LDL (low density lipoprotein e.g., bad cholesterol), bilirubin, ALT (alanine amino transferase, also called SGPT), liver damage, ALP (alkaline phosphatase), Hgb (Hemoglobin), white blood cells, basophiles, monocytes, higher count with allergies eosinophils, lymphocytes higher count with leukemia, higher count with infection neutrophils, etc.

An exemplary device may perform tests for so-called heart damage markers or cardiac enzymes. The blood test most commonly used to confirm the existence of heart muscle damage is the creatine kinase (CK). A small fraction of the CK enzyme, CK-MB, is often measured as well. CK-MB shows an increase above normal in a person's blood test about six hours after the start of a heart attack. It reaches its peak level in about 18 hours and returns to normal in 24 to 36 hours. The peak level and the return to normal can be delayed in a person who's had a large heart attack, especially without early and aggressive treatment.

Tests may measure the level of other cardiac muscle proteins called troponins, specifically troponin T (cTnT) and troponin I (cTnI). These proteins control the interactions between actin and myosin, which contracts or squeezes the heart muscle. Troponins specific to heart muscle have been found, allowing the development of blood tests (assays) that can detect minor heart muscle injury ("microinfarction") not detected by CK-MB. Normally the level of cTnT and cTnI in the blood is very low. It increases substantially within several hours (on average four to six hours) of muscle damage. It peaks at 10 to 24 hours and can be detected for up to 10 to 14 days.

With respect to techniques, an implantable microarray device may use extraction fluid techniques (e.g., suction effusion techniques, wick Extraction), optical techniques (e.g., near infrared spectroscopy, infrared spectroscopy, Fourier transform infrared spectrometry, nuclear magnetic resonance spectroscopy, scatter changes, polarization changes, dielectrophoresis, competitive fluorescence sensors, etc.), source opportunities (interstitial fluids, sweat, urine, blood cells, plasma), etc.

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. An implantable microarray device comprising:
   an inlet for a body fluid;
   one or more splitter channels coupled to the inlet, the splitter channels being adapted to divide the body fluid into smaller volumes;
   a plurality of individual reaction cell arrays coupled to the one or more splitter channels, wherein each reaction cell array comprises a series of reaction cells configured to receive the body fluid;
   a sensor array to sense a reaction result for an individual reaction cell array wherein the reaction result corresponds to a reaction between the body fluid and at least one reagent in each of the reaction cells of the individual reaction cell array; and
   a positioning mechanism to position an individual reaction cell array with respect to the sensor array.

2. The implantable microarray device of claim 1 wherein the sensor array outputs a binary value.

3. The implantable microarray device of claim 2 wherein the binary value corresponds to a range of concentrations for a component in the body fluid.

4. The implantable microarray device of claim 1 wherein each reaction cell is pre-filled with at least one reagent.

5. The implantable microarray device of claim 1 wherein each reaction cell is pre-filled with at least one reagent in a dry state.

6. The implantable microarray device of claim 1 wherein each reaction cell is pre-filled with at least one reagent in gel form.

7. The implantable microarray device of claim 1 wherein the sensor array comprises an emitter to emit radiation and a detector to detect radiation.

8. The implantable microarray device of claim 1 wherein the sensor array senses fluorescence.

9. The implantable microarray device of claim 1 further comprising a refillable reservoir for a reagent.

10. The implantable microarray device of claim 1 further comprising a waste reservoir.

11. The implantable microarray device of claim 1 wherein the reaction result corresponds to a heart damage marker.

12. A method comprising:
   receiving patient data;

prescribing one or more tests based at least in part on the patient data;

providing a plurality of reaction cell arrays each comprising a series of reaction cells configured to perform the one or more prescribed tests;

implanting the plurality of reaction cell arrays in the patient; and acquiring test data corresponding to the one or more tests by using a sensor array configured to sense an individual reaction cell array.

13. The method of claim 12 wherein each of the reaction cells comprises at least one reagent for performing a prescribed test.

14. The method of claim 13 wherein the prescribed test comprises a test for a heart damage marker.

15. A method comprising:
providing an in vivo array of reaction cells;
implanting the array in the patient;
filling at least some of the reaction cells with a body fluid;
reacting the body fluid in each of the reaction cells with at least one reagent;
detecting a reaction cell result for each of the reaction cells wherein each of the reaction cell results is a binary value; and
determining an overall result based on the binary values.

16. The method of claim 15 wherein the overall result corresponds to a concentration range.

17. The method of claim 15 wherein the filling occurs according to a schedule.

18. The method of claim 15 wherein the filling occurs at a time based at least in part on a prior overall result.

19. The method of claim 15 further comprising communicating a result to an ex vivo device.

20. An implantable microarray device comprising:
an inlet for a body fluid;
one or more splitter channels coupled to the inlet, the splitter channels being adapted to divide the body fluid into smaller volumes;
a plurality of individual reaction cell arrays coupled to the one or more splitter channels, wherein each reaction cell array comprises a series of reaction cells configured to receive the body fluid;
a sensor array to sense a reaction result for an individual reaction cell array wherein the reaction result corresponds to a reaction between the body fluid and at least one reagent in each of the reaction cells of the individual reaction cell array; and
a pressure driven mechanism to cause flow of body fluid to one or more of the reaction cell arrays.

* * * * *